(12) United States Patent
Aleksandrova et al.

(10) Patent No.: US 8,535,923 B2
(45) Date of Patent: Sep. 17, 2013

(54) ENCAPSULATED LIVER CELL COMPOSITION

(75) Inventors: Krasimira Aleksandrova, Hanover (DE); Peter Pediaditakis, Raleigh, NC (US); Jo Salisbury, Garner, NC (US); Wolfgang Rüdinger, Birkenau (DE)

(73) Assignee: Cytonet GmbH & Co. KG (DE)

( * ) Notice: Subject to any disclaimer, the term of this patent is extended or adjusted under 35 U.S.C. 154(b) by 0 days.

(21) Appl. No.: 13/263,352

(22) PCT Filed: Apr. 27, 2010

(86) PCT No.: PCT/EP2010/002563
§ 371 (c)(1),
(2), (4) Date: Dec. 13, 2011

(87) PCT Pub. No.: WO2010/124837
PCT Pub. Date: Nov. 4, 2010

(65) Prior Publication Data
US 2012/0093937 A1    Apr. 19, 2012

Related U.S. Application Data

(63) Continuation-in-part of application No. 12/430,330, filed on Apr. 27, 2009, now abandoned.

(51) Int. Cl.
*C12N 11/10*    (2006.01)
*A61K 9/14*    (2006.01)
*A01N 65/00*    (2009.01)

(52) U.S. Cl.
USPC ................... 435/178; 424/491; 424/93.7

(58) Field of Classification Search
USPC ..................... 435/178; 424/491, 93.7
See application file for complete search history.

(56) References Cited

U.S. PATENT DOCUMENTS

| 4,377,513 | A | 3/1983 | Sugimoto et al. | |
|---|---|---|---|---|
| 4,956,128 | A | 9/1990 | Hommel et al. | |
| 5,084,350 | A | 1/1992 | Chang et al. | |
| 2008/0031850 | A1* | 2/2008 | Bader | 424/85.2 |
| 2011/0172150 | A1 | 7/2011 | Bader | 514/7.7 |

FOREIGN PATENT DOCUMENTS

| EP | 0148605 | 7/1985 |
|---|---|---|
| EP | 0205564 B2 | 12/1986 |
| EP | WO 95/05465 | 12/1986 |
| EP | 0411678 | 2/1991 |
| JP | 54-55790 | 5/1979 |
| JP | 57-040411 | 3/1982 |
| JP | 2007-517001 | 6/2007 |
| WO | WO 86/03520 | 6/1986 |
| WO | WO 94/25055 | 11/1994 |
| WO | WO 2004/009766 A2 | 1/2004 |
| WO | WO 2005/063965 A1 | 7/2005 |
| WO | WO 2007/046719 A2 | 4/2007 |

OTHER PUBLICATIONS

Hu et al. Critical Care Medicine 23(7):1237-1242, 1995.*
International Search Report dated Dec. 27, 2010, issued in corresponding international application No. PCT/EP2010/002563.
Tasima Haque et al: "In vitro study of alginate-chitosan microcapsules: an alternative to liver cell transplants for the treatment of liver failure", Biotechnology Letters, Springer Netherlands, vol. 27, No. 5, Mar. 1, 2005, pp. 317-322, XP019231110, ISSN: 1573-6776, DOI: DOI: 10.1007/S10529-005-0687-3 the whole document.
Ponce S et al: "In vivo evaluation of EPO-secreting cells immobilized in different alginate-PLL microcapsules", Journal of Controlled Release, Elsevier, Amsterdam, NL, vol. 116, No. 1, Nov. 10, 2006, pp. 28-34, XP024957682, ISSN: 0168-3659, DOI: DOI:10.1016/J.JCONREL.2006.08.024 [retrieved on Nov. 10, 2006 J the whole document.
Chandrasekaran, et al., "Functional Analysis of Encapsulated Hepatic Progenitor Cells," Tissue Engineering, vol. 12, No. 7, (Nov. 7, 2006), p. 2001.
Graber, et al., "Erythropoietin and the Control of Red Cell Production," Ann. Rev. Med., vol. 29 (1978), pp. 51-66.
Wrighton, et al., "Small Peptides as Potent Mimetics of the Protein Hormone Erythropoietin," Science, vol. 273 (Jul. 26, 1996), pp. 458-463.
Miyake, et al., "Purification of Human Erythropoietin," The Journal of Biological Chemistry, vol. 252, No. 15 (Issue of Aug. 10, 1977), pp. 5558-5584.
English language translation of Japanese Notice of Reasons for Rejection dated May 17, 2013 in corresponding Japanese Patent Application No. 2012-506407.
English language translation of Russian Office Action dated Mar. 28, 2013 in corresponding Russian Patent Application No. 2011148106/15(072162).
Chandan Guha et al. Hepatocyte transplantation and Liver-Directed Gene Therapy// Landes.Bioscience; 2000, Data List [on-line] 2000 [found Feb. 12, 2013] found from the Internet, URL: http://www.ncbi.nlm.nih.gov/books/NBK6159/,specification, p. 3).
Singapore Examination Report prepared by Hungarian Patent Office dated Jul. 2, 2013 in Application No. 201107837-5 corresponding to U.S. Appl. No. 13/263,352. (1 page).
Gao Y. et al. "Microencapsulating Hepatocytes" Transplantation Proceedings, vol. 37, No. 10, pp. 4589-4593 (Dec. 1, 2005) (5 pages).
US 4,487,758, 12/1984, Goosen et al. (withdrawn)

* cited by examiner

*Primary Examiner* — Marcia S Noble
(74) *Attorney, Agent, or Firm* — Ostrolenk Faber LLP

(57) ABSTRACT

Microcapsules including a capsule shell encapsulating a suspension of a therapeutically effective amount of liver cells in physical contact with a liver cell stimulating amount of erythropoietin.

12 Claims, 1 Drawing Sheet

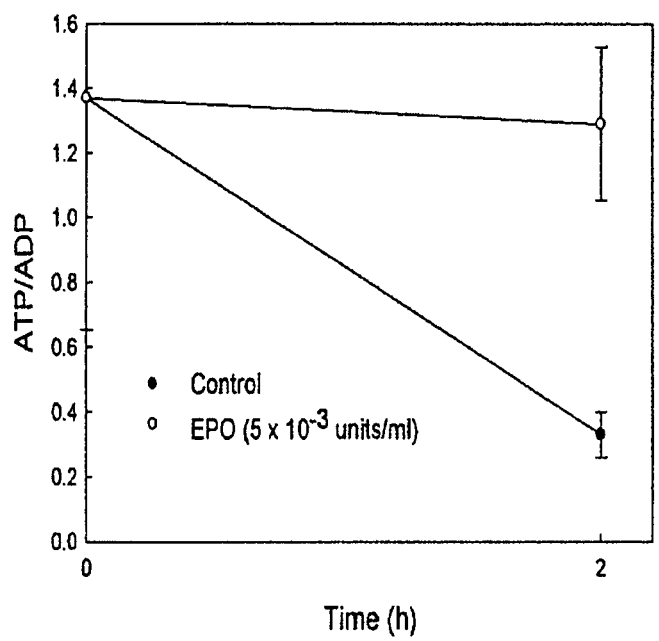

ENCAPSULATED LIVER CELL COMPOSITION

CROSS REFERENCE TO RELATED APPLICATIONS

The present application is a 35 U.S.C. §371 National Phase conversion of PCT/EP2010/002563, filed Apr. 27, 2010, which claims benefit of U.S. application Ser. No. 12/430,330, filed Apr. 27, 2009, the disclosure of which is incorporated herein by reference. The PCT International Application was published in the English language.

TECHNICAL FIELD

The present invention relates to microcapsules comprising liver cells and erythropoietin, methods to prepare said microcapsules and methods to treat a patient comprising applying said microcapsules to the patient.

BACKGROUND

Although the liver of a healthy subject is able to regenerate itself by repairing or replacing injured or ill tissue, unfortunately once a certain amount of liver cells has died or has severely been damaged through disease or injuries, the whole organ may fail. Such a failure, be it an acute or chronic failure, may cause disease and death. The therapy of liver diseases encompasses conventional means, such as the administration of drugs. However, it is also state of the art to trans-plant livers or parts thereof. Furthermore, it is widely known to transplant liver cell populations in patients, such as described for instance in WO 2004/009766 A2. It is, however, still a major challenge in devising therapies for curing acute or chronic hepatic diseases to deliver liver cells to a patient in need thereof which methods are optimized in terms of viability, engraftment, proliferation and differentiation of the transplanted liver cells in the target tissue.

Hague et al. (Biotechnology Letters 27 (5) (2005), 317-322)) describe in vitro studies of alginate-chitosan microcapsules as an alternative to liver cell transplants for the treatment of liver failure. Chandrasekaran et al. (Tissue Engineering 12 (7), (2006)) disclose hepatic progenitor cells embedded in electrostatically produced beads.

In spite of the efforts to develop therapeutic systems which efficiently deliver liver cells into the patient's target tissue, there still remains the need to provide more reliable therapeutic means to cure liver diseases, in particular means which provide a high viability and physiological activity of the liver cells in the target body.

SUMMARY

The present teaching solves said problem by providing microcapsules comprising a capsule shell, preferably a biocompatible capsule shell, encapsulating a suspension of a therapeutically effective amount of liver cells in physical contact to a liver cell stimulating amount of erythropoietin. In a preferred embodiment the present invention provides microcapsules comprising a capsule shell and a core, wherein the capsule shell encapsulates in the core a suspension of a therapeutically effective amount of liver cells and a liver cell stimulating amount of erythropoietin, in particular wherein the erythropoietin (in the following termed EPO) and the liver cells are in physical contact to each other so as to provide a stimulating effect of the EPO to the liver cells.

Thus, in a preferred embodiment the present invention foresees to provide microcapsules comprising a capsule shell, preferably made from a biocompatible capsule shell material, and a core being enveloped by said capsule shell. In one preferred embodiment of the present invention the core contains a suspension of a therapeutically effective amount of liver cells in physical contact to a liver cell stimulating amount of erythropoietin.

In another preferred embodiment the core contains a matrix, preferably made from a biocompatible matrix material, wherein the suspension of the therapeutically effective amount of liver cells is embedded in said matrix in physical contact to a liver cell stimulating amount of erythropoietin. Preferably, the material of the matrix is the same as the capsule shell material. In another embodiment the biocompatible matrix material may be another material than the capsule shell material.

Thus, the present invention provides the teaching to encapsulate both erythropoietin and liver cells together in a biocompatible capsule shell such that the erythropoietin is in physical contact to the liver cells so as to exert at least one of its biological functions on the liver cells, in particular in stimulating the liver cells.

One advantage of the present invention is that the liver cells are encapsulated in the capsule shell and therefore do not elicit any adverse reaction, in particular allergic or immunological reaction, in the patient, in which the microcapsule is preferably transplanted. Furthermore, the close contact of the erythropoietin to the liver cell stimulates said liver cells to perform their biological function so as to provide the patient with the biological functions of a liver.

In a particularly preferred embodiment the liver cells are contained in the microcapsule in such a concentration so as to be in physical contact to each other providing an even more pronounced effect when stimulated by the erythropoietin. Thus, the invention foresees in a particularly preferred embodiment that the liver cells contained in the microcapsules are in physical contact to each other and are in physical contact to the erythropoietin.

DETAILED DESCRIPTION

In the context of the present invention the expression "liver cells are in physical contact to erythropoietin" means that erythropoietin is able to exert at least one of its biological functions on the liver cell, in particular is able to reach and being reversibly or irreversibly bound by the receptors for erythropoietin present on the liver cell.

In the context of the present invention the expression "liver cells being in physical contact to each other" means that the liver cells are present in the microcapsule of the present invention in such a close vicinity to each other that the cells touch each other and provide a stable environment closely resembling the natural physiological situation in a liver.

In the context of the present invention the term "stimulating the liver cells" means that the erythropoietin increases the biological functionality of the liver cells, preferably in the patient in which the microcapsule is transplanted, increases the viability of the liver cells, increases their storage stability and/or increases their potential to successfully perform their biological function once being transplanted in the subject.

In the context of the present invention "biocompatibility" means that the material, in particular the capsule shell material and/or the matrix material is able to keep the integrated liver cells viable and allow the interaction between the erythropoietin and the liver cells. In a particularly preferred embodiment the term "biocompatible" means that the material allows, preferably a long-term, implantation in a patient while still retaining the function of the embedded liver cells without eliciting any undesirable local or systemic effect in the subject, in particular allergic and immunological reactions. In a particularly preferred embodiment the term "biocompatible" means that the material is able to perform as a substrate supporting the liver cell activity including the solicitation of molecular and mechanical similar system between the liver cells and the EPO, preferably in order to optimize liver regeneration without eliciting any undesirable effects in the cells and the subject.

In the context of the present invention the term "erythropoietin" designates a glycoprotein hormone that controls erythropoieses or blood cell production, preferably a substance that, in appropriately dosage, controls the growth, differentiation and maturation of stem cells via erythroblasts to erythrocytes.

Erythropoietin is a glycoprotein having 166 amino acids, three glycosylation sites and a molecular weight of about 34,000 Da. During EPO-induced differentiation of erythrocyte progenitor cells, globin synthesis is induced, synthesis of the heme complex is augmented and the number of ferritin receptors is increased. Thereby the cell can take up more iron and synthesize functional hemoglobin. In mature erythrocytes, hemoglobin binds oxygen. Thus the erythrocytes and the hemoglobin contained therein play a key role in supplying oxygen to the organism. These processes are initiated through the interaction of EPO with an appropriate receptor on the cell surface of the erythrocyte progenitor cells (Graber and Krantz, Ann. Rev. Med. 29 (1978), 51-56).

In the context of the present invention the term "erythropoietin" both encompasses the wild type erythropoietin, in particular the human erythropoietin, and derivatives therefrom. In the context of the present invention derivatives of erythropoietin are recombinant erythropoietin proteins which are characterized by at least one amino acid deviation, in particular deletion, addition or substitution of one more amino acid compared to the wild type EPO, and/or erythropoietin proteins with a different glycosylation pattern compared to the wild type erythropoietin. In a particularly preferred embodiment erythropoietin derivatives are also fusion proteins or truncated proteins of wild type erythropoietin or derivatives thereof. In a particularly preferred embodiment a derivative of erythropoietin is also a wild type erythropoietin having a different glycosylation pattern compared to the wild type glycosylation pattern.

The term "erythropoietin" used here includes EPO of every origin, especially human or animal EPO. The term used here thus encompasses not only the naturally occurring, or in other words wild-type forms of EPO, but also its derivatives, also termed modifications, muteins or mutants, as long as they exhibit the biological effects of wild-type erythropoietin.

In connection with the present invention, there will be understood by "derivatives" also those derivatives of erythropoietin that, while retaining the basic erythropoietin structure, are obtained by substitution of one or more atoms or molecular groups or residues, especially by substitution of sugar chains such as ethylene glycol, and/or whose amino acid sequences differ from that of the naturally occurring human or animal erythropoietin protein in at least one position but essentially have a high degree of homology at the amino acid level and comparable biological activity. Erythropoietin derivatives which can be employed, for example, in the present invention are known from WO 94/25055, EP 0148605 B1 or WO 95/05465.

"Homology" means especially a sequence identity of at least 80%, preferably at least 85% and particularly preferably at least more than 90%, 95%, 97% and 99%. The term "homology" known by the person skilled in the art thus refers to the degree of relationship between two or more polypeptide molecules. This is determined by the agreement between the sequences. Such agreement can mean either identical agreement or else a conservative exchange of amino acids.

According to the invention, the term "derivative" also includes fusion proteins, in which functional domains of another protein are present on the N-terminal part or on the C-terminal part. In one embodiment of the invention, this other protein may be, for example, GM-CSF, VEGF, PlGF, a statin or another factor that has a stimulating effect on endothelial progenitor cells. In a further embodiment of the invention, the other protein may also be a factor that has a stimulating effect on liver cells.

The differences between an erythropoietin derivative and native or wild type erythropoietin may arise, for example, through mutations such as deletions, substitutions, insertions, additions, base exchanges and/or recombinations of the nucleotide sequences coding for the erythropoietin amino acid sequences. Obviously such differences can also be naturally occurring sequence variations, such as sequences from another organism or sequences that have mutated naturally, or mutations introduced selectively into the nucleic acid sequences coding for erythropoietin, using common means known in the art, such as chemical agents and/or physical agents. In connection with the invention, therefore, the term "derivative" also includes mutated erythropoietin molecules, or in other words erythropoietin muteins.

According to the invention, peptide or protein analogs of erythropoietin may also be used. In connection with the present invention, the term "analogs" includes compounds that do not have any amino acid sequence identical to the erythropoietin amino acid sequence but have a three-dimensional structure greatly resembling that of erythropoietin, so that they have comparable biological activity. Erythropoietin analogs may be, for example, compounds that contain, in a suitable conformation, the amino acid residues responsible for binding of erythropoietin to its receptors, and that are therefore able to simulate the essential surface properties of the erythropoietin binding region. Compounds of this type are described, for example, in Wrighton et al., Science, 273 (1996), 458.

The EPO used according to the invention can be produced in various ways, for example by isolation from human urine or from the urine or plasma (including serum) of patients suffering from aplastic anemia (Miyake et al., J. B. C. 252 (1977), 5558). As an example, human EPO can also be obtained from tissue cultures of human renal cancer cells (JA Unexamined Application 55790/1979), from human lymphoblast cells, which have the ability to produce human EPO (JA Unexamined Application 40411/1982), and from a hybridoma culture obtained by cell fusion of a human cell line. EPO can also be produced by methods of gene technology, using suitable DNA or RNA coding for the appropriate amino acid sequence of EPO to produce the desired protein by genetic engineering, for example in a bacterium, in a yeast, or in a plant, animal or human cell line. Such methods are described, for example, in EP 0148605 B2 or EP 0205564 B2 and EP 0411678 B1.

In the context of the present invention derivatives of erythropoietin are in a preferred embodiment functional and clinically proven EPO derivatives, preferably selected from the group consisting of Epoetin, also termed Procrit, Epogen, Eprex or NeoRecormon, Epoetin delta, also termed Dynepo, Darbepoetin, also called Aranesp, PDpoetin, CERA (continuous erythropoietin receptor antagonist) and methoxy polyethylene glycol-epoetin beta, also termed Mircera.

In a preferred embodiment of the present invention a microcapsule is a, preferably spherical, bead made from a biocompatible capsule shell material which contains embedded therein the therapeutically effective amount of liver cells in physical contact to a liver cell stimulating amount of erythropoietin. In the context of the present invention a microcapsule is preferably a sphere, preferably with a diameter from 10 µm to 10 mm, preferably 140 µm to 10 mm, preferably 50 µm to 1 mm, preferably 60 µm to 800 µm, preferably 100 to 700 µm. In a preferred embodiment of the present invention the microcapsules of the present invention consist of the liver cells, the erythropoietin and the biocompatible capsule shell material. Preferably in addition to the above three elements a coating of the microcapsule and/or a biocompatible matrix in the core of the microcapsule is foreseen.

Thus, in a particularly preferred embodiment the present invention relates to microcapsules comprising a therapeutically effective amount of liver cells encapsulated in a biocompatible matrix material in physical contact to a liver cell stimulating amount of erythropoietin.

In a particularly preferred embodiment, the liver cells are embedded in the capsule shell in form of a suspension, preferably in a cell culture suspension. The liver cell suspension is preferably in form of liver cells contained in a cell culture medium or in a physiologically acceptable aqueous solution. The liver cell suspension is preferably a suspension of liver cells in a cell culture medium.

In a particularly preferred embodiment, the liver cells are embedded in the matrix contained in the shell in form of a suspension, preferably in a cell culture suspension, preferably in form of liver cells contained in a cell culture medium or in a physiologically acceptable aqueous solution.

In a particularly preferred embodiment the present invention relates to microcapsules, wherein the liver cells are selected from the group consisting of hepatic precursor cells, hepatic stem cells, hepatoblasts and hepatocytes.

In a particularly preferred embodiment the present invention relates to microcapsules, wherein the liver cells are selected from the group consisting of hepatic precursor cells, hepatic stem cells, hepatoblasts, hepatocytes and endothelial cells.

In a furthermore preferred embodiment the present invention relates to microcapsules, wherein the liver cells are obtained from adult liver, embryogenic liver, fetal liver, neonatal liver or liver cell cultures. Preferably, the liver cells are living liver cells. In a preferred embodiment, the liver cells may be obtained from a living or a dead, in particular a recently deceased, donor.

In a furthermore preferred embodiment the present invention relates to microcapsules, wherein the liver cells are human liver cells, non-human primate liver cells, pig liver cells, dog liver cells, cat liver cells, rabbit liver cells, mouse liver cells or rat liver cells.

In a particularly preferred embodiment the present invention relates to microcapsules, wherein the microcapsules have an average diameter from 100 to 700 µm, preferably from 200, 300, 400, 500, 600 or 650 to 700 µm.

In a particularly preferred embodiment the present invention relates to microcapsules, wherein the therapeutically effective amount of liver cells is $10^4$ to $10^8$, preferably $10^5$ to $10^7$ liver cells/ml suspension.

In a particularly preferred embodiment the present invention relates to microcapsules, wherein the liver cells have an average diameter of 8 to 14 µm, preferably 9 to 12 µm.

In a furthermore preferred embodiment the present invention relates to microcapsules, wherein the liver cell stimulating amount of erythropoietin is $10^{-7}$ to $10^{-2}$, preferably $10^{-7}$ to $10^{-3}$, preferably $10^{-7}$ to $10^{-5}$ and preferably $10^{-8}$ to $10^{-5}$ U/ml suspension.

In a furthermore preferred embodiment the present invention relates to microcapsules, wherein the EPO is wild type erythropoietin or recombinant erythropoietin.

In a furthermore preferred embodiment the present invention relates to microcapsules, wherein the capsule shell material is selected from the group consisting of alginate, alginate-chitosan (AC), alginatepoly-L-lysine (APA), thermogelation-polymer and PEG-hydrogel.

In a furthermore preferred embodiment the present invention relates to microcapsules, wherein the matrix material is selected from the group consisting of alginate, alginate-chitosan (AC), alginate-poly-L-lysine (APA), thermogelation-polymer and PEG-hydrogel.

In a furthermore preferred embodiment the present invention relates to microcapsules, wherein in addition to the liver cells at least one further cell type is present in the microcapsule.

In a particularly preferred embodiment the at least one further cell type present in the microcapsule is selected from the group consisting of liver stellate cells, biliary cells, hemopoietic cells, monocytes, macrophage lineage cells, lymphocytes and endothelial cells.

In a furthermore preferred embodiment of the present invention it is foreseen that the microcapsule comprises in addition to the liver cells and the EPO at least one further growth factor, preferably selected from the group consisting of HGH (human growth factor), VEGF (vascular endothelial growth factor), CSF (colony stimulating factor), thrombopoietin, SCF complex (Skpcollien, F-box containing complex), SDF (stromal cell-derived factor-1), NGF (nerve growth factor), PIGF (phosphatidyl inositol glycan anchor biosynthesis, class F), HMG coreductase inhibitor, ACE (angiotensin converting enzyme) inhibitor, AT-1-inhibitor and an NO donor.

In a particularly preferred embodiment the present invention relates to microcapsules, wherein the microcapsules are coated.

In a particularly preferred embodiment of the present invention, the coating is a polymer coating, a sugar coating, a sugar alcohol coating and/or a fat or wax coating.

In a furthermore preferred embodiment the present invention relates to a method for preparing the microcapsules according to the above comprising:
  a) providing a suspension of a therapeutically effect amount of liver cells and a liver cell stimulating amount of erythropoietin,
  b) mixing the suspension of the liver cells and the erythropoietin to bring them in physical contact to each other and
  c) encapsulating the suspension of the liver cells and the erythropoietin in a capsule shell material so as to form the microcapsule.

In a furthermore preferred embodiment the present invention relates to a method, wherein the microcapsules obtained in step c) are cryopreserved.

In a furthermore preferred embodiment the present invention relates to a method for the prophylactic or therapeutic treatment of a liver disease in a subject in need thereof comprising administering the microcapsules according to the present invention to the subject in need thereof.

In a particularly preferred embodiment the present invention relates to a method, wherein the liver disease is hepatitis, cirrhosis, inborn errors of metabolism, acute liver failure, acute liver infections, acute chemical toxicity, chronic liver failure, cholangiocitis, biliary cirrhosis, Alagille syndrome, alpha-1-antitrypsin deficiency, autoimmune hepatitis, biliary atresia, cancer of the liver, cystic disease of the liver, fatty liver, galactosemia, gallstones, Gilbert's syndrome, hemochromatosis, hepatitis A, hepatitis B, hepatitis C and other hepatitis viral infections, poryphyria, primary sclerosing cholangitis, Reye's syndrome, sarcoidosis, tyrosinemia, type 1 glycogen storage disease or Wilson's disease.

In a furthermore preferred embodiment the present invention relates to a method, wherein the administration is effected by introduction of the microcapsules under the liver capsule, into the spleen, into the liver, into the liver pulp or into the spleenic artery or portal vein.

In a furthermore preferred embodiment the present invention relates to a method for introducing liver cells into a subject comprising administering the microcapsules according to the present invention into the subject.

In a particularly preferred embodiment of the present invention the administration is effected by introduction into the subject in need thereof, wherein the administration is a topical, enteral or parenteral administration. In a preferred embodiment the topical administration is an epicutaneous, inhalational, vaginal or internasal administration. In a preferred embodiment the enteral administration is by mouth, by gastric feeding tube or rectally. In a preferred embodiment the parenteral administration is by injection or infusion, preferably intervenous, intraarterial, intramuscular, intracardiac, subcutaneous, intraosseous, intradermal, intrathecal, intraperitoneal or intravesical administration. In a furthermore preferred embodiment the parenteral administration is transdermal, transmucosal or inhalational.

In a furthermore preferred embodiment the present invention relates to a method for cultivating liver cells in a culture medium, preferably in vitro, comprising culturing microcapsules according to the present invention in a suitable culture medium and under conditions suitable for maintaining or increasing viability of the liver cells.

In a particularly preferred embodiment the present invention relates to a method for maintaining or increasing the energy state of liver cells in a culture medium, preferably in vitro, comprising culturing microcapsules according to the present invention in a suitable culture medium and under conditions suitable for maintaining or increasing the energy state of the liver cells.

Further preferred embodiments of the present invention are the subject matter of subclaims.

BRIEF DESCRIPTION OF THE DRAWING

The FIGURE shows the ATP/ADP ratio of liver cells encapsulated with or without EPO after culture as a measure of the cell's energy state.

EXAMPLES

The following Example is provided only for the purpose of illustrating the invention and it should not be deemed to limit the invention in any manner.

Example 1

Liver cells, in the presence of EPO ($5\times10^{-3}$ units/ml), encapsulated with alginate at a concentration of $10^4$ to $10^8$ cells/ml into beads with an average diameter of 100 to 700 μm will fare better than liver cells encapsulated identically except without EPO. The ATP/ADP ratio is used as a measure of the cell's energy state. If the ATP/ADP ratio is increased during the course of the experiment at a faster rate or remains higher than in the untreated cells, then this evidence would support the hypothesis.

Encapsulation of Liver Cells

Cell encapsulation of liver cells from a single stock of cryopreserved human liver cells was performed using an electrostatic bead generation apparatus. Liver cells were suspended in routine culture medium and mixed with 2% sodium alginate solution in a 1:1 ratio. The resulting 1% alginate solution containing liver cells at a concentration of 4 million cells/ml was drawn into a 1-cc syringe fitted with a 24-gauge angiocatheter. The angiocatheter was pierced at the hub with a 23-gauge needle to serve as the positive electrode in the electrostatic casting process. The syringe was loaded onto a syringe pump (Braintree Scientific BS-8000, Braintree, Mass.) and arranged such that the droplets ejected from the angiocatheter would fall orthogonally onto the surface of a 125 mM calcium chloride ($CaCl_2$) solution (conventional or Cytonet buffer 4 with 1% human albumin, with $5\times10^{-3}$ and $5\times10^{-6}$ U/ml EPO or without EPO) in a 250 ml glass beaker. The distance from the angiocatheter tip to the surface of a $CaCl_2$ was fixed at approximately 2.5 cm. Pump flow rates were set within the range of 0.75 to 1.5 ml/min. A grounded electrode was immersed in the $CaCl_2$ receiving bath. An electrostatic potential was developed across the angiocatheter tip and $CaCl_2$ bath using a high-voltage DC source (Spellman model RHR30PF30, Hauppauge, N.Y.) in the range of 3.8 to 6 kV. Bead size (500 μm) was controlled by adjusting the applied potential. When the syringe pump was turned on in the presence of the high electrostatic potential, the expressed sodium alginate solution was pulled away as tiny droplets that polymerize into solid calcium alginate immediately upon contact with the $CaCl_2$ solution.

After encapsulation the liver cell alginate beads were kept in William's E supplemented with 10% serum, 244 unit/ml penicillin, 0.244 mg/ml, 5.5 mM glutamine, 0.195 units/ml insulin, 0.017 ug/ml glucagon, 0.73 ug/ml prednisolon, 0.54 ug/ml dexamethason and cultured for 2 hours.

De-encapsulation was done by placing beads in 100 mM citrate. When the alginate was dissolved, cells were washed twice with PBS and pelleted by 200×G for one minute. Metabolites were extracted by placing 4% perchloric acid on the cells and homogenizing for 20 seconds with a hand held micro homogenizer. The sample was then centrifuged at 14,000×G for three minutes and the supernatant, with the metabolites, was removed. The perchloric acid was neutralized with KOH and the insoluble potassium perchlorate was removed by centrifugation. The sample was then analyzed by an HPLC method for ATP, ADP analysis described in "Measurements of ATP in Mammalian Cells" (Manfredi et al. Methods 2002 (4), 317-326). Three parallel plates were used to perform the ATP/ADP level determination.

Results

The ATP/ADP ratio is a measure of the cell's energy and represents the effect of all biochemical pathways on the metabolic state of the cells. The maintenance of the ATP/ADP ratio (see FIGURE) seen in liver cells encapsulated with EPO clearly shows that the cells are able to maintain energy generating pathways which are required for every function of the cells. In this experiment, the ratio of ATP/ADP was maintained in the EPO-treatment group but not in the untreated controls. While the EPO-treated group was able to maintain the ATP/ADP ratio, the ATP/ADP ratio in controls dropped below 0.5. This shows that EPO may be signalling through a non-EPO receptor driven pathway to afford the cell trophic stimulation.

What is claimed is:

1. Microcapsules comprising a capsule shell encapsulating a suspension of a therapeutically effective amount of liver cells in physical contact with a liver cell stimulating amount of erythropoietin, wherein the therapeutically effective amount of liver cells is from $10^4$ to $10^8$ liver cells/ml suspension and the liver cell stimulating amount of erythropoietin is $10^{-7}$ to $10^{-2}$ U/ml suspension.

2. The microcapsules according to claim 1, wherein the liver cells are selected from the group consisting of hepatic precursor cells, hepatic stem cells, hepatoblasts, endothelial cells and hepatocytes.

3. The microcapsules according to claim 1, wherein the liver cells are obtained from adult liver, embryogenic liver, fetal liver, neonatal liver or liver cell cultures.

4. The microcapsules according to claim 1, wherein the liver cells are human liver cells, non-human primate liver cells, pig liver cells, dog liver cells, cat liver cells, rabbit liver cells, mouse liver cells or rat liver cells.

5. The microcapsules according to claim 1, wherein the microcapsules have an average diameter from 100 to 700 μM.

6. The microcapsules according to claim 1, wherein the liver cells have an average diameter of 8 to 14 μm.

7. The microcapsules according to claim 1, wherein said erythropoietin is wild type erythropoietin or recombinant erythropoietin.

8. The microcapsules according to claim 1, wherein the capsule shell is made from a biocompatible material selected from the group consisting of alginate, alginate-chitosan (AC), alginate-poly-L-lysine (APA), thermogelation-polymer and PEG-hydrogel.

9. The microcapsules according to claim 1, wherein in addition to the liver cells at least one further cell type is present in the microcapsule.

10. The microcapsules according to claim 1, wherein the microcapsules are coated.

11. The microcapsules according to claim 1, wherein the microcapsule contains the liver cells and the erythropoietin embedded in a biocompatible matrix.

12. The microcapsules according to claim 1, wherein the liver cell stimulating amount of erythropoietin is $10^{-7}$ to $10^{-3}$ U/ml suspension.

* * * * *